United States Patent [19]

Brake

[11] Patent Number: 5,268,507
[45] Date of Patent: Dec. 7, 1993

[54] PREPARATION OF AMIDE DERIVATIVES OF HYDROXY ACIDS

[75] Inventor: Loren D. Brake, Wilmington, Del.

[73] Assignee: E. I. Du Pont de Nemours and Company, Wilmington, Del.

[21] Appl. No.: 796,272

[22] Filed: Nov. 22, 1991

[51] Int. Cl.$^5$ ............................................. C07C 233/05
[52] U.S. Cl. ..................................... 564/203; 564/201; 549/274; 549/273; 549/347; 549/475; 525/938; 544/170
[58] Field of Search ................ 564/203, 201; 549/274, 549/273, 475, 347; 525/938

[56] References Cited

U.S. PATENT DOCUMENTS

| | | | |
|---|---|---|---|
| 2,773,852 | 12/1956 | Rowe et al. | 564/203 |
| 3,284,417 | 11/1966 | Hostettler et al. | 260/78.3 |
| 3,578,700 | 5/1971 | Klootwijk et al. | 260/484 |
| 4,727,163 | 2/1988 | Bellis | 549/274 |
| 4,797,468 | 1/1989 | De Vries | 528/354 |
| 4,835,293 | 5/1989 | Bhatia | 549/274 |

FOREIGN PATENT DOCUMENTS

| | | | |
|---|---|---|---|
| 0338565 | 10/1989 | European Pat. Off. | 564/203 |
| 9001521 | 2/1990 | PCT Int'l Appl. | |

OTHER PUBLICATIONS

Maulding et al., CA 104:230322b, 1986 (abstract only).

*Primary Examiner*—Glennon H. Hollrah
*Assistant Examiner*—Shailendra Kumar

[57] ABSTRACT

Depolymerizing high molecular weight polyhydroxy acid by reacting with an amine to produce an amide derivative.

16 Claims, No Drawings

PREPARATION OF AMIDE DERIVATIVES OF HYDROXY ACIDS

BACKGROUND OF THE INVENTION

1. Field of the Invention

The present invention relates to the depolymerization of polyhydroxy acid (PHA) by an amine to prepare an amide derivative of hydroxy acids. More specifically, the present invention relates to the recovery of hydroxy acid value from a polyhydroxy acid polymer-containing source such as food container trash.

2. Description of the Related Art

Shaped articles of high molecular weight (at least 10,000, and normally 15,000 to 500,000 MW) polyhydroxy acid (PHA), particularly as polylactic acid (PLA, polylactide), and polyglycolic acid (PGA, polyglycolide), and copolymers thereof, have been known for years. An important property of these polymers is that they are slowly hydrolyzable and thereafter biodegradable to environmentally benign by-products. Consequently high molecular weight PHA polymer shaped articles are finding increasing application as replacements for polystyrene and other non-degradable polymers in products that will degrade in a landfill, such as fast food containers (Sinclair et al., WO90/01521, Feb. 22, 1990).

While this is a significant step in minimizing litter and long-term landfill disposal, discarding high molecular weight polyhydroxy acid articles for natural destruction by hydrolysis has the cost penalty of discarding the valuable polyhydroxy acid.

Although the hydrolysis of PHAs is well known, heretofore it has not been achievable in a time frame to permit recovery from other insoluble ingredients and reuse of the valuable hydroxy acid (HA) moieties. In fact, although degradable, the time for degradation of high molecular weight PHAs is so long as not to offer a significant lessening burden on landfills.

Thus, there is a need for an economical method to recover and recycle the polyhydroxy acid content of this source of insoluble waste material and avoid burdening landfills with this waste.

The most economical routes for PHA production start with the acid such as lactic acid. The acid is converted to an ester, dimerized to a cyclic ring such as lactide, which is then polymerized to PHA. This is a complicated and costly process. See Bhatia U.S. Pat. No. 4,835,293 (May 30, 1989); Bellis U.S. Pat. No. 4,727,163 (Feb. 23, 1988); Klootwijk U.S. Pat. No. 3,578,700 Hostettler et al. U.S. Pat. No. 3,284,417; and De Vries U.S. Pat. No. 4,797,468 (Jan. 10, 1989).

Bhatia, U.S. Pat. No. 5,136,057, discloses the depolymerization of low molecular weight oligomers remaining after PHA polymerization. This patent application does not address the problem of recovery of the monomeric values from used high molecular weight PHA articles.

Copending and commonly assigned U.S. patent application Ser. Nos. 07/797,502, 07/797,503, 07/796,273 and 07/796,274 disclose the recovery of PHAs, respectively, in the presence of an alcohol and an acid catalyst; in the presence of water and acid; in water under heat and pressure; and in the presence of water and lower alkyl alcohol.

The aforementioned patents and patent applications are incorporated herein by reference.

SUMMARY OF THE INVENTION

The present invention provides a method of depolymerizing polyhydroxy acid to an amine derivative comprising mixing said polymer to be depolymerized with an amine represented by the formula $HNR_1R_2$ wherein $R_1$ and $R_2$ can be the same or different and are selected from the group consisting of hydrogen and alkyls of 1–4 carbon atoms while maintaining the reaction mixture at sufficient temperature and pressure for a sufficient time to depolymerize. In one embodiment of the invention the polymer is selected from group consisting of polylactide, polyglycolide, and polymers containing a major proportion of polylactide or polyglycolide copolymerized with up to 30% of another monomer selected from the group consisting of epsilon-caprolactone, delta-valerolactone, 1,5-dioxepen-2-one, 1,4-dioxan-2-one, beta-butyrolactone, beta-propiolactone, 6-methyl-2,5-morpholinedione and mixtures thereof. Typically the temperature of the process is in the range 20° to 120° C. and the time is in the range of ¼ to 16 hours.

The present invention further provides a process for recovering hydroxy acid value from a polyhydroxy acid polymer-containing source comprising the steps of:

(a) contacting a polyhydroxy acid polymer-containing material, wherein said polyhydroxy acid polymer-containing material is contaminated with or constitutes trash, with an amine represented by the formula $HNR_1R_2$ wherein $R_1$ and $R_2$ can be the same or different and are selected from the group consisting of hydrogen and alkyls of 1–4 carbon atoms while maintaining the polymer/catalyst mixture at sufficient temperature and pressure for a sufficient time to depolymerize said polymer and form an amide; and (b) thereafter isolating and recovering said amide.

DESCRIPTION OF THE PREFERRED EMBODIMENTS

The present invention relates to an inexpensive depolymerization of high molecular weight PHAs in the preparation of useful amine derivatives, particularly amides. In the process of the present invention PHA is mixed with an amine and adequate heat and pressure are applied, to raise the temperature to that needed to depolymerize the particular PHA. When depolymerization is completed to the desired extent, amine derivative and any excess amine can be recovered by distillation, under vacuum if needed.

When adequate amine is used, normally at least a slight excess of the molar amine derivative requirements, depolymerization conversion in excess of 60%, and normally in the range of 70–90%, of theoretical is achieved, leaving a heel rich in PHA equivalents. If desired this heel, with or without the addition of new PHA, can be sequentially reprocessed one or more times with further additions of amine. By this series of treatments, substantially 100% conversion of PHA to the amine derivative can be achieved.

This process is used for the depolymerization of the common PHAs, and co- and ter-polymers therewith. It is effective with polymers of at least 10,000 molecular weight, the preferred range being from 15,000 to 500,000 or higher. It is most useful in the depolymerization of polylactide, polyglycolide and copolymers thereof; also it is useful for PHAs containing these polymer moieties polymerized with other monomers. These co- and ter-polymers preferably contain at least 70% of PLA and PGA moities, and not more than 30% of the other monomer. Examples of other suitable monomer units are:
epsilon-caprolactone,
delta-valerolactone,
1,5-dioxepan-2-one,
1,4-dioxan-2-one,
beta-butyrolactone,
beta-propiolactone, and
6-methyl-2,5-morpholinedione.

The particular other monomer units present in the PHA to be depolymerized are not critical, the present process having wide applicability in depolymerizing and recovering the monomer value of PHAs.

The amines useful in the present process are of the formula $HNR_1R_2$ wherein $R_1$ and $R_2$ can be the same or different and are selected from the group consisting of hydrogen and lower alkyls of 1-4 carbon atoms. The preferred amines are ammonia, monomethylamine and dimethylamine. The amine may be used heat or dissolved in an inert solvent selected from the group consisting of water and alkyl alcohols containing 1-4 carbon atoms. The most preferred process comprises the use of aqueous ammonia reacted with polylactic acid, yielding a solution of lactamide in water that can easily be separated from insoluble nonreactive residues from fast food containers.

The amount and type of amine used affects the time required to carry out the depolymerization and the percent conversion. Normally a molar ratio of amine to PHA (on an acid unit basis) in the range of 1:1 to 2:1 is used. Since an excess of amine favors depolymerization, preferably a substantial excess is used, but not so much as to make amine recovery an excessive expense.

Increased amine content, and temperature all speed up the depolymerization. In many cases overall economies and reaction kinetics dictate depolymerizing at atmospheric pressure although elevated pressure sometimes is needed to reach the necessary temperature for depolymerization. However, it may be desirable to use elevated pressures, up to about 1000 psi, when depolymerization of the particular PHA and amine derivative requires such pressure, or when high depolymerization rate at elevated temperatures is desired. Normally autogenous pressure is adequate. Temperatures in the range of 20°-200° C. or higher, preferably 50°-125° C. are employed.

A very important economical aspect of the present process is the speed of the depolymerization. By selecting optimal reaction conditions, batch depolymerizations of significant quantities of PHA can be depolymerized often in 1 hour and even in as little as 15 minutes. Reactor design, i.e., agitation, etc., also plays an important role in reaction rate. Where speed is less a factor than other economies, batch times as long as 16 hours may be appropriate.

Continuous process depolymerization is also possible, such as with the feed polymer and amine being continuously introduced into the first depolymerization stage of a multistage system, and the amine derivative product and excess unreacted amine being recovered from the last stage, or from intermediate points.

EXAMPLE 1

A mixture of 75 grams polylactide (300,000 MW) and 90 grams of 60% dimethylamine in water is heated at 75° C. for one hour in a pressure vessel under autogenous pressure. The liquid product is distilled at atmospheric pressure to remove the water and continued under vacuum to give a 50% yield of N,N-dimethyl lactamide (b.p. 79.6° C. at 4 mm).

EXAMPLE 2

Example 1 is repeated using 60 grams anhydrous dimethylamine in place of the 60% aqueous dimethylamine. Distillation gives a 75% yield to N,N-dimethyl lactamide.

EXAMPLE 3

A mixture of 75 grams polylactide, 50 grams methanol and 50 grams anhydrous monomethyl amine is heated at 75° C. for 45 minutes in a pressure vessel under autogenous pressure. The liquid product is distilled to recover N-methyl lactamide.

EXAMPLE 4

A mixture of 75 grams polylactide (300,000 MW) and 100 grams 28% ammonium hydroxide is heated for one hour in a pressure vessel under autogenous pressure at 75° C. The product is a clear homogenous liquid consisting of lactic acid and soluble low molecular weight oligomers.

EXAMPLES 5-8

The process of Example 4 is repeated using the following polymers with similar results:
5. Copolymer of 80% lactic acid and 20% glycolic acid
6. Copolymer of 90% lactic acid and 10% glycolic acid
7. Copolymer of 80% lactic acid and 20% epsilon-caprolactone
8. Copolymer of 90% lactic acid and 10% beta-propiolactone.

EXAMPLES 9-12

The process of Example 2 is repeated using the following amines at the given temperatures and times with similar results:

| Example | Amine | Temperature | Hold Time |
|---|---|---|---|
| 9 | n-butyl amine | 150° C. | 30 minutes |
| 10 | diethyl amine | 100° C. | 45 minutes |
| 11 | isopropyl amine | 50° C. | 2 hours |
| 12 | n-propyl amine | 175° C. | 20 minutes |

EXAMPLE 13

A mixture of polylactide and 100 grams 28% ammonium hydroxide is held at 30° C. with agitation in a sealed bottle for 15 hours. The polylactide depolymerize to a clear solution.

What is claimed is:

1. The process of depolymerizing polyhydroxy acid polymer having a molecular weight of at least 10,000, to an amide comprising mixing said polymer to be depolymerized with an amine, said amine represented by the formula $HNR_1R_2$, wherein $R_1$ and $R_2$ are independently selected from the group consisting of hydrogen and alkyls of 1-4 carbon atoms, while maintaining the reaction mixture at sufficient temperature and pressure for a sufficient time to depolymerize said polyhydroxy acid and form said amide.

2. The process of claim 1 wherein the polymer contains at least a major proportion of polylactide.

3. The process of claim 1 wherein said polymer is selected from group consisting of polylactide, polyglycolide, and polymers containing a major proportion of polylactide or polyglycolide copolymerized with up to 30% of another monomer selected from the group consisting of epsilon-caprolactone, delta-valerolactone, 1,5-dioxepen-2-one, 1,4-dioxan-2-one, beta-butyrolactone, beta-propiolactone, 6-methyl-2,5-morpholinedione and mixtures thereof.

4. The process of claim 1 wherein the polymer is polylactide.

5. The process of claim 1 wherein said temperature is in the range of 20°-200° C. and high enough to depolymerize said polymer.

6. The process of claim 1 wherein the time is in the range of ¼-16 hours.

7. The process of claim 1 wherein said amine derivative is an amide.

8. The process of claim 1 wherein the amine to polyhydroxy acid molar ratio is in the range of 1:1 to 2:1.

9. The process of claim 1 wherein the amine is ammonia.

10. The process of claim 1 wherein the amine is monomethylamine.

11. The process of claim 1 wherein the amine is dimethylamine.

12. The process of claim 9 wherein the product of depolymerization is lactamide.

13. The process of claim 1 wherein the remaining heel is reprocessed by further heating after adding more of said amine to the heel.

14. The process of claim 1 wherein polymer and amine are continuously added and amine derivative product and unreacted amine are continuously removed.

15. The process of claim 1 additionally comprising the step of recovering said amide.

16. The process of claim 15 wherein said amide is recovered by distillation.

* * * * *